(12) United States Patent
O'Donnell, Jr.

(10) Patent No.: US 6,413,968 B1
(45) Date of Patent: Jul. 2, 2002

(54) TREATMENT OF MYASTHENIA GRAVIS BY CYCLIC NUCLEOTIDE PHOSPHODIESTERASE INHIBITION

(76) Inventor: Francis E. O'Donnell, Jr., 709 The Hamptons La., St. Louis, MO (US) 63017

( * ) Notice: Subject to any disclaimer, the term of this patent is extended or adjusted under 35 U.S.C. 154(b) by 0 days.

(21) Appl. No.: 09/606,818

(22) Filed: Jun. 30, 2000

(51) Int. Cl.⁷ .................... A61K 31/505; A61K 31/50
(52) U.S. Cl. ................ 514/252.16; 514/269; 514/274; 514/903; 514/907
(58) Field of Search ........................... 514/252.16, 269, 514/274, 903, 907

(56) References Cited

U.S. PATENT DOCUMENTS 6,136,810 A * 10/2000 Takayama et al. .......... 514/258
6,204,383 B1 * 3/2001 Lu et al. .................... 544/262

* cited by examiner

*Primary Examiner*—Frederick Krass
(74) *Attorney, Agent, or Firm*—Paul M. Denk

(57) ABSTRACT

A method of treating myasthenia gravis confined to the eyes iby administering, orally, a therapeutically effective dose the nucleotide (cGMP) phosphodiesterase inhibitor Sildenafil either 100 mg. once a day, or 25 mg. four times a day. The object of this oral therapy being the alleviation of myasthenic complications such as diplopia and ptosis.

2 Claims, 1 Drawing Sheet

TREATMENT OF MYASTHENIA GRAVIS BY CYCLIC NUCLEOTIDE PHOSPHODIESTERASE INHIBITION

FIELD OF THE INVENTION

The present invention relates to the treatment of myasthenia gravis and, in particular, to the treatment of the ocular involvement in myasthenia gravis.

INTRODUCTION

Myasthenia gravis is a neuromuscular conduction defect that is responsible for progressive weakening of skeletal muscle strength, involvement of the extraocular muscles and levator palpebral and results in diplopia and ptosis. Diplopia, in particular, can be disabling. In about 50% of cases, myasthenia gravis is limited to ocular involvement. There is evidence suggesting that "ocular myasthenia gravis" may have a pathogenesis that is related but somewhat different from "systemic myasthenia gravis."

In strictly ocular myasthenia gravis, for example, there is a male preponderance, relatively lower incidence of anti-acetylcholine receptor antibody and significantly lower serum titers, relatively poor response to anticholinesterase agents alone and a reasonable response to corticosteroids.

In myasthenia gravis, as a result of an autoimmune process, the acetylcholine receptors at the myoneural junction are reduced in number. In prior art treatment of myasthenia gravis, an anti-cholinesterase agent is used to increase the effect of acetylcholine at the myoneural junction despite the reduction in receptor density. Studies with parasympathetic enervation of smooth muscle have shown that stimulation by acetylcholine results in a rapid, large increase in cyclic GMP (guanosine $3^1,5^1$—cyclic monophosphate) in the muscle cell.

Whereas therapy for systemic myasthenia gravis typically includes anti-cholinesterase agents, the relative lack of efficacy in controlling ocular involvement has been perplexing and frustrating. The present invention discloses a novel therapeutic intervention, especially for ocular involvement, in myasthenia gravis.

OBJECTS OF THE PRESENT INVENTION

It is an object of the present invention to provide an effective oral therapy for alleviation of myasthenic complications such as diplopia and ptosis.

It is an object of the present invention to treat myasthenia gravis without dependence upon anti-cholinesterase agents.

It is an object of the present invention to treat ocular involvement in myasthenia gravis without dependence on anti-cholinesterase agents.

It is an object of the present invention to increase cGMP concentration in muscles without dependence upon anti-cholinesterase agents.

PREFERRED EMBODIMENTS

Figure 1:
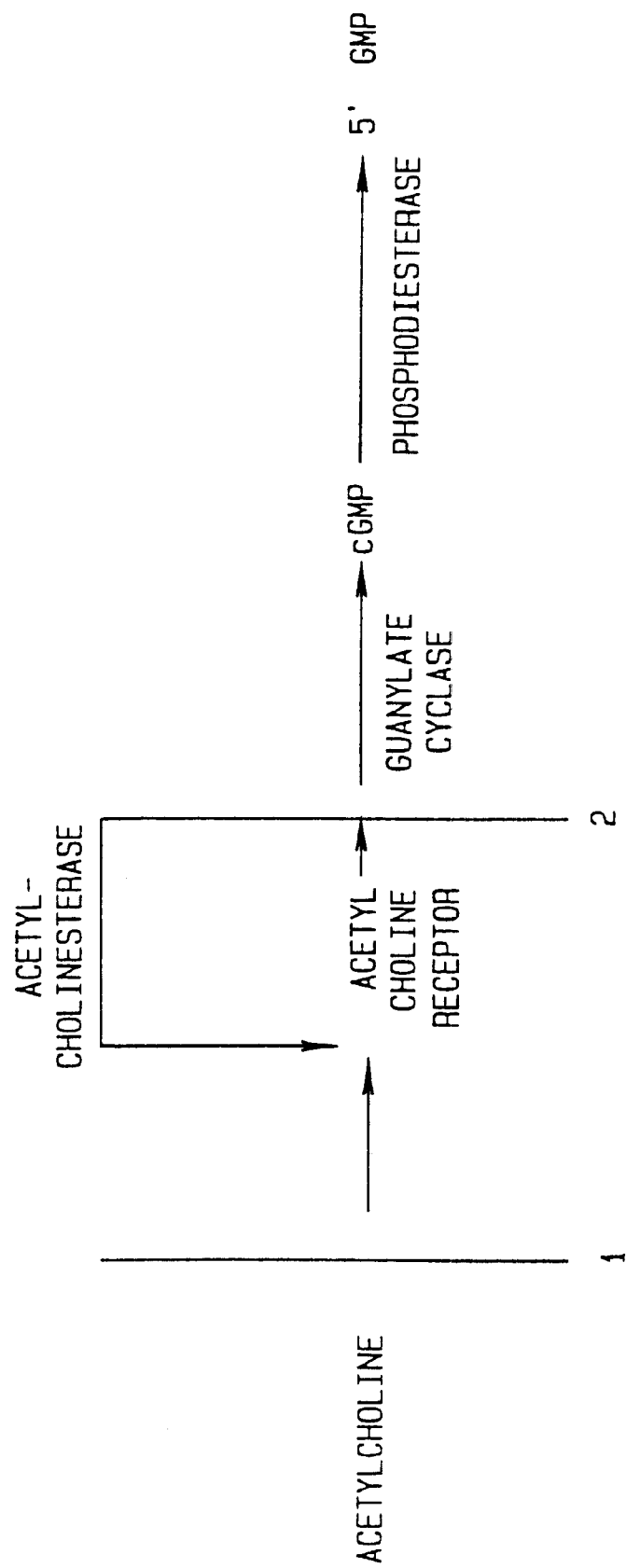
FIG. 1 is a schematic of the myoneural junction which shows how acetylcholine normally increases cGMP concentration.

It is a preferred embodiment of the present invention to increase cGMP concentrations by means other than acetylcholinesterase inhibition.

It is a preferred embodiment of the present invention to increase cGMP in myasthenic muscle by administration of a therapeutically effective dose of an inhibitor of cyclic nucleotide phosphodiesterase.

It is a preferred embodiment of the present invention to increase cGMP in muscle tissue by administration of a therapeutically effective dose of a cyclic nucleotide phosphodiesterase inhibitor.

DETAILED DESCRIPTION

I have discovered that the use of a cyclic nucleotide phosphodiesterase inhibitor causes more normal muscle function, especially in the extraocular muscle of myasthenic patients. Moreover, the use of a cyclic nucleotide phosphodiesterase inhibitor potentiates the effects of acetylcholinesterase inhibitors for skeletal muscle treatment in myasthenic gravis.

There are at least seven different types of cyclic nucleotide phosphodiesterase (PDE). Their primary substrates vary (e.g., cGMP vs. cAMP) and their concentrations vary by tissue type. Inhibitors of each type can have a crossover inhibition of other types. For example, cGMP-specific PDE5 inhibitors in the penis can block PDE6 activity in photoreceptors. The present invention teaches the use of inhibitors of phosphodiesterase that have sufficient cGMP specificity in muscle tissue to effect a beneficial increase in cGMP and, hence, in muscle function.

FIG. 1 shows the acetylcholine released from the nerve cell membrane (1), traverses the extracellular space to attach to acetylcholine receptors on the muscle cell membrane (2). Here, acetylcholinesterase acts to remove acetylcholine. Acetylcholine receptor activity results in stimulation of cGMP levels, probably through guanylate cyclase activity. cGMP is then metabolized by a cyclic nucleotide phosphodiesterase to $5^1$-GMP. In the present invention, a cyclic nucleotide phosphodiesterase is used to increase cGMP levels independently of acetylcholinesterase inhibition.

EXAMPLES

A 27-year-old African-American male presented with a three-week history of vertical diplopia that was incomitant and right ptosis. An anti-cholinesterase, Mestinon, 60 mg three times daily had failed to relieve the diplopia or the ptosis. Exam revealed a right hypotropia and ptosis. Sildenafil, a known cGMP-specific phosphodiesterase inhibitor, 25 mg tab four times daily was prescribed, and within 24 hours, there was immediate resolution of dipolopia and ptosis.

Variations or modifications to the subject matter of this invention may occur to those skilled in the art upon review of the disclosure provided herein. Such variations or modifications, if within the spirit of this invention, are intended to be encompassed within the scope of any claims to patent protection issuing upon this development. The description of the preferred embodiment as provided in this application is done so for illustrative purposes only.

Having thus described the invention, what is claimed and desired to be secured by Letters Patent is:

1. A method for treating ocular myasthenia gravis, comprising administering to an individual an effective amount of a cGMP phosphodiesterase inhibitor, said amount being administered orally, said effective amount of said inhibitor being about 100 mg. per day, administered in at least one dose or in a dosage of about 25 mg. four times a day.

2. The method of claim 1 wherein the cGMP phosphodiesterase inhibitor is Sildenafil.

* * * * *